(12) United States Patent
Cewers

(10) Patent No.: US 6,357,671 B1
(45) Date of Patent: Mar. 19, 2002

(54) ULTRASONIC NEBULIZER

(75) Inventor: Göran Cewers, Lund (SE)

(73) Assignee: Siemens Elema AB, Solna (SE)

(*) Notice: Subject to any disclaimer, the term of this patent is extended or adjusted under 35 U.S.C. 154(b) by 0 days.

(21) Appl. No.: 09/489,835

(22) Filed: Jan. 24, 2000

(30) Foreign Application Priority Data

Feb. 4, 1999 (SE) .............................................. 9900369

(51) Int. Cl.⁷ ............................ B05B 1/08; A61M 11/06
(52) U.S. Cl. ........................ 239/102.2; 239/67; 239/69; 239/71; 239/99; 239/102.1; 239/338
(58) Field of Search ............................ 239/67, 69, 71, 239/73, 99, 102.1, 102.2, 338

(56) References Cited

U.S. PATENT DOCUMENTS

| | | |
|---|---|---|
| 3,839,651 A | 10/1974 | Michaels |
| 3,918,640 A * | 11/1975 | Piccino et al. ....... 239/102.2 X |
| 4,300,131 A | 11/1981 | Mitsui et al. |
| 4,319,155 A | 3/1982 | Nakai et al. |
| 4,641,053 A * | 2/1987 | Takeda ................ 239/102.2 X |
| 4,776,990 A | 10/1988 | Verity |
| 5,217,165 A * | 6/1993 | Takahashi et al. ....... 239/102.2 |
| 5,303,585 A | 4/1994 | Lichte |
| 5,361,989 A * | 11/1994 | Merchat et al. .......... 239/102.2 |
| 5,429,302 A * | 7/1995 | Abbott ..................... 239/102.2 |

FOREIGN PATENT DOCUMENTS

| | | |
|---|---|---|
| EP | 0 151 753 A2 | 12/1984 |
| EP | WO 93/09409 | 5/1993 |
| EP | 0 845 663 A1 | 11/1997 |
| JP | 9-173978 | 7/1997 |

* cited by examiner

*Primary Examiner*—Robin O. Evans
(74) *Attorney, Agent, or Firm*—Schiff Hardin & Waite

(57) ABSTRACT

An ultrasonic nebulizer includes a nebulization chamber for holding a liquid to be nebulized, the liquid being limited by an upper boundary within the chamber, and a nebulization source acoustically couplable to the liquid within the chamber to provide therein an ultrasonic output at an amplitude to cause nebulization. The nebulization source is controllable to vary the amplitude of the ultrasonic output to provide a measurement period during which no nebulization occurs, and a sonar device measures, during the measurement period, a time interval between emission of an acoustic pulse toward the boundary and detection of a component of the emitted acoustic pulse reflected from the boundary, and provides an output signal dependent on the measured time interval for use in determining location information of the boundary within the chamber.

8 Claims, 2 Drawing Sheets

ULTRASONIC NEBULIZER

BACKGROUND OF THE INVENTION

1. Field of the Invention

The present invention relates to an ultrasonic nebulizer (atomizer) and in particular to a nebulizer of the type having an output controllable dependent on the level of liquid available for nebulization.

2. Description of the Prior Art

Ultrasonic nebulizers are devices which utilize a source of ultrasound, such as for example a piezoelectric crystal oscillator, acoustically coupled to a liquid in a nebulizing chamber in order to generate an aerosol of small liquid droplets in a space above the liquid boundary. The generated aerosol may be used for any desired purpose such as humidification or medication. Such nebulizers are often used as a component in a breathing circuit of a mechanical ventilator, where they are employed in the delivery of controlled doses of anaesthetic or other additive into a breathing gas for supply to a patient.

It is important, particularly in the medical field, to be able to monitor the level of liquid in the nebulizing chamber. This may be for example, in order to maintain a supply of liquid throughout mechanical ventilation or to monitor the dosage of liquid delivered into the breathing gas.

One known ultrasonic nebulizer which is provided with a liquid level indicator is disclosed in U.S. Pat. No. 3,839,651. This nebulizer uses a temperature sensitive resistance element which is thermally coupled to the liquid within the nebulizing chamber. The current in an electrical circuit containing this element is dependent on the amount of liquid within the chamber and is used to decrease power supplied to the oscillator and to provide a visible indication when the liquid level falls to a predetermined minimum. One problem with such a level indicator is that it is relatively insensitive to small changes in liquid level which are likely to occur between successive, or closely spaced, inspiration periods of a patient breathing cycle.

SUMMARY OF THE INVENTION

An object of the present invention is to provide an ultrasonic nebulizer having a level indicator capable of sensing such small changes.

The above object is achieved in accordance with the principles of the present invention in a nebulizer having a nebulization chamber containing a liquid to be nebulized the liquid having an upper boundary within the chamber, and an ultrasonic nebulization source which is acoustically coupled to the liquid to introduce ultrasound into the liquid to nebulizer the liquid, and wherein the ultrasonic nebulization source is operated to emit ultrasound with a variable amplitude so as to provide a measurement period during which no nebulization occurs, and wherein the nebulizer has a sonar device which, during the measurement period, measures a time interval between emission of an acoustic pulse toward said liquid boundary and detection of a component of the emitted acoustic pulse reflected from the boundary so as to produce an output signal dependent on this measured time interval which is indicative of a location of the upper boundary of the liquid within the nebulization chamber.

By controlling the amplitude of the nebulization source to provide periods where no nebulization occurs, possibly by providing periods of zero amplitude output, a sonar device which employs echo ranging techniques may be used to measure the location of the upper boundary of the liquid within the nebulization chamber. This provides a relatively sensitive arrangement for identifying changes in the location of the liquid boundary from which, for example, the amount of liquid within the nebulization chamber may be calculated.

Preferably, a single piezoelectric crystal is employed as both the nebulization source and as the sonar device. This allows existing nebulizing chambers and sources to be used with only modifications to the electronic circuitry used to control the crystal being necessary. Moreover, by using only one crystal, a major component cost saving is achieved compared with employing separate sonar and nebulization sources.

A difference forming circuit is used to enable differences in the location of the liquid boundary to be determined. The determined difference, for example, may be used to monitor the amount of liquid nebulizer between measurement periods or to monitor the effect of different known crystal driving currents on the liquid boundary during a single measurement period. Both of these monitoring modes then may be employed to calibrate the nebulization source and to control the amplitude or duration of the ultrasonic output from the source to, for example, more reliably provide a required amount of nebulization or to remove power from the source if a minimum liquid level is reached.

Particularly useful is the latter mode of monitoring since a calibration of the output of the nebulization source may be made before generating any nebulized liquid.

DESCRIPTION OF THE PREFERRED EMBODIMENTS

Figure 1:
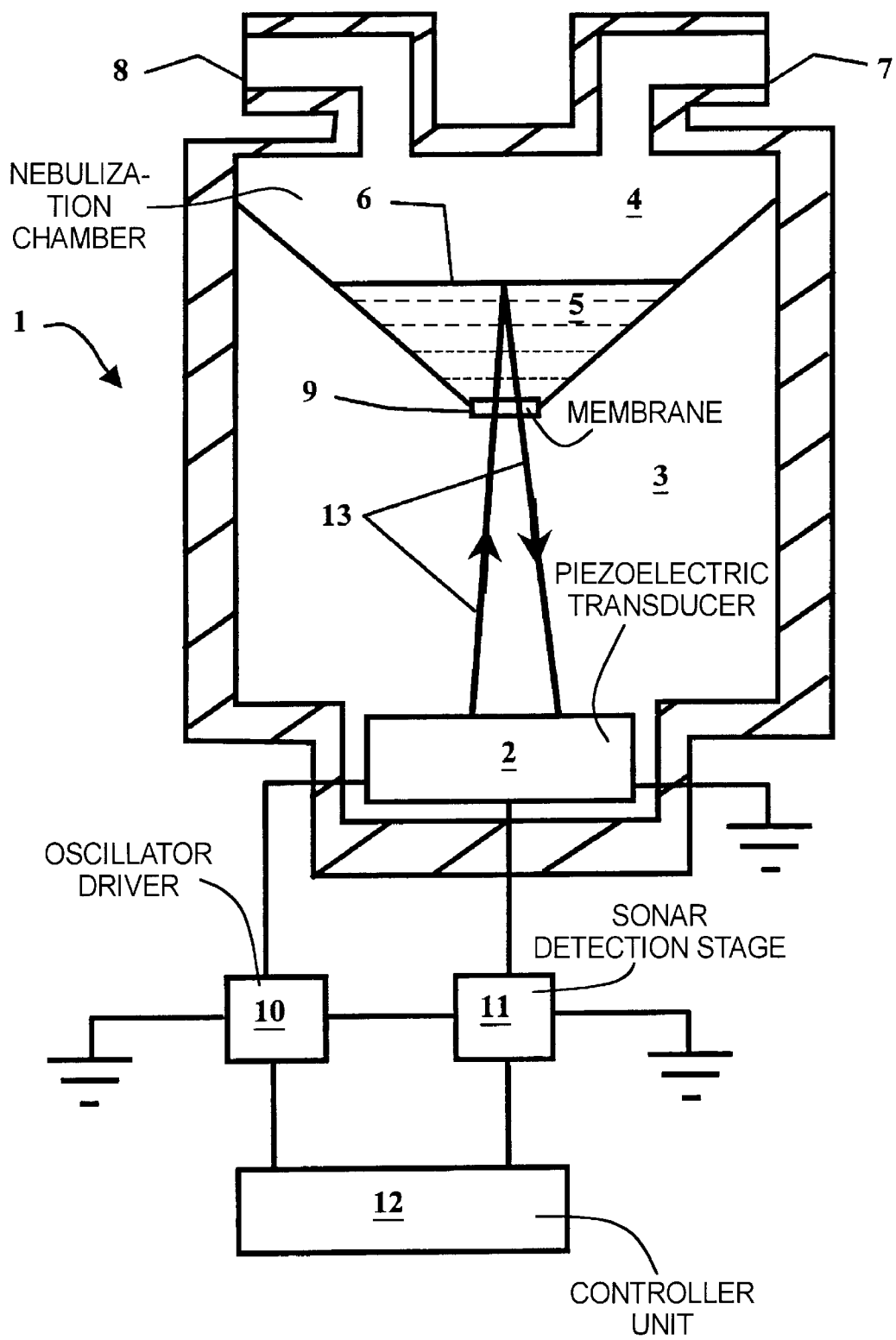
FIG. 1 is a schematic representation of an embodiment of a nebulizer and illustrates one mode of operation according to the present invention.
Figure 2:
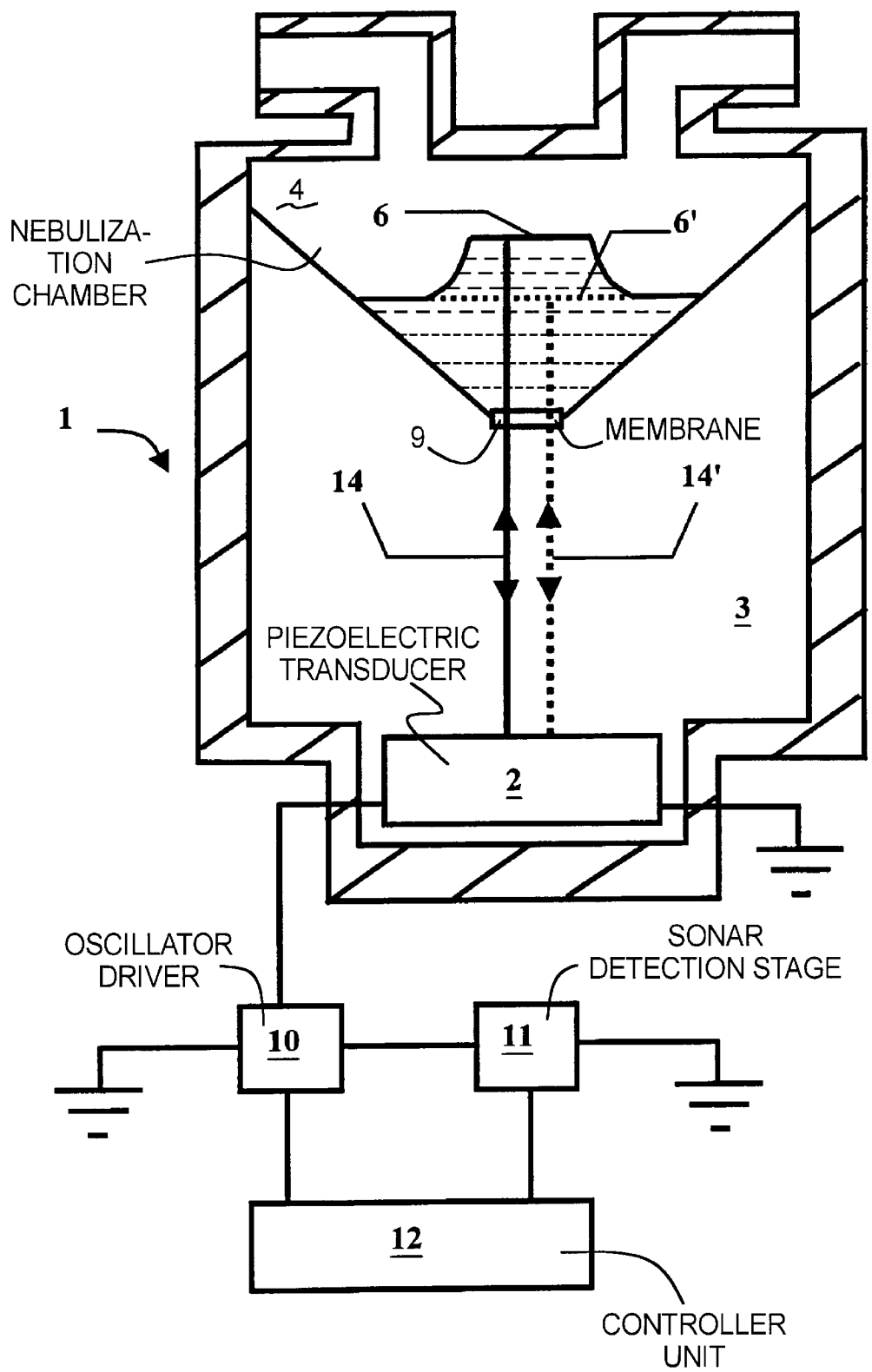
FIG. 2 is a schematic representation of a nebulizer illustrating a further mode of operation according to the present invention.

In FIGS. 1 and 2 an ultrasonic nebulizer is shown generally at 1. The nebulizer 1 of FIGS. 1 and 2 has the same basic components but different modes of operation, which modes will be described separately for each of the FIGS. 1 and 2.

The ultrasonic nebulizer 1 of FIGS. 1 and 2 includes a ultrasonic oscillator 2, here in the form of a piezoelectric transducer, which is located in a water chamber 3 above which is a nebulization chamber 4. A liquid 5 for nebulization is held within the nebulization chamber 4 so that in use a space into which nebulized liquid passes remains in the chamber 4 above an upper boundary 6 of the liquid 5. Gas may be introduced into the nebulization chamber 4, flowing from an inlet 7 to an outlet 8 through the space above the upper boundary 6, and removing from the chamber 4 liquid droplets formed during nebulization. A thin membrane 9 separates the water chamber 3 from the nebulization chamber 4 so that ultrasonic energy from the oscillator 2 can pass readily therethrough with the result that the oscillator 2 "sees" essentially only a single body of liquid, terminating at the upper boundary 6. An oscillator driver 10 is connected in an electrical circuit with the oscillator 2 and is arranged to drive the oscillator 2 to generate a controllable, variable amplitude ultrasonic signal for emission into the water chamber 3. A sonar detection stage 11 is also provided in electrical connection with the oscillator driver 10 and with the oscillator 2. The detection stage 11 includes conventional timer circuitry (not shown) which is arranged to measure the transit time for an ultrasonic sonar pulse to travel from the oscillator 2 to the upper liquid boundary 6 and back again. The detection stage 11 is also adapted to emit a signal representative of this measured transit time.

The driver 10 and the sonar detection stage 11 are readily realizable by those skilled in the art using conventional electrical engineering methodology and an understanding of the principles of their function, as provided herein.

A controller unit 12, for example in the form of a suitably programmed computer, is operably connected to both the driver 10 and the sonar detection stage 11 and provides control of the driver 10 and calculates the location of the upper liquid boundary 6 within the nebulization chamber 4 from the output signal of the sonar detection stage 11.

To explain the nebulizer 1 of FIG. 1 and its mode of operation, the arrows 13 show the path of the sonar pulse. In use the controller unit 12 provides control instructions to the driver 10 for generating a periodic variation in the amplitude of the ultrasonic energy emitted by the oscillator 2. The variation is such that nebulization periods, during which high amplitude ultrasound are emitted which are sufficient to cause nebulization, alternate with measurement periods, during which only ultrasound sonar pulses are emitted having an amplitude, insufficient to affect i.e. disturb, the location of the upper boundary 6 to a measurable extent.

During a measurement period a trigger signal is sent to the sonar detection stage 11, corresponding to the oscillator 2 being driven, to generate an ultrasonic sonar pulse. The trigger signal, which may conveniently be provided either by the controller unit 12 or the driver 10, initiates the start of timing by the timer circuitry. The time measurement is stopped when the receipt of a reflected component of the generated ultrasonic pulse is detected at the oscillator 2. This detection is facilitated by the use of a piezoelectric transducer as the oscillator 2. It is well known that ultrasonic energy incident on such a piezoelectric transducer 2 can cause detectable changes in the electrical properties of an electrical circuit in which the transducer 2 is included. Thus in the present embodiment the receipt of the reflected pulse is detected using such known circuitry within the detection stage 11. The pulse emission and detection optionally can be carried out a number of times throughout the measurement period and an average location determination made within the controller unit 12 based on the averaged value of the measured transit times. The determined location may be used within the controller unit 12 to provide a control signal which inhibits the operation of the driver 10 when a location corresponding to a minimum level is detected.

Optionally, the controller unit 12 may be programmed to compare the currently determined location with a previously determined location, having a known temporal relationship to the currently determined location and preferably one made in a consecutive measurement period, so that the amount of liquid nebulized during an intervening nebulization period or periods may be calculated within the controller unit 12 to provide dose information. This dose information may then be used by the controller unit 12 in the control of the driver 10 to regulate one or both of the amplitude of the ultrasound generated for nebulization and the duration of the nebulization period to obtain a desired dose from the nebulizer 1.

For explaining the nebulizer 1 of FIG. 2 and its mode of operation, solid arrows 14 and dashed arrows 14' show paths of the sonar pulses. In use the controller unit 12 controls the driver 10 to provide the piezoelectric transducer 2 with a known, variable amplitude driving force to generate a corresponding variable amplitude ultrasonic output into the water chamber 3. The driver 10 is controlled to provide from the oscillator 2 at least one nebulization period, during which high amplitude ultrasound is emitted sufficient to cause nebulization, and at least one measurement period, during which ultrasound is emitted at amplitudes lower than are capable of causing nebulization.

During each measurement period the controller unit 12 controls the driver 10 to generate at least two different amplitudes of ultrasound to provide distinguishable and different locations of at least part of the upper boundary 6, 6'. As illustrated in FIG. 2 one output amplitude is chosen so as not to affect (i.e. disturb) the location of the upper boundary 6' to a measurable extent, for example a zero amplitude output, and the other output amplitude is chosen to provide a localized change in the upper boundary 6. The sonar detection stage 11 and the driver 10 operate cooperatively to provide two measurements of transit times; one for a sonar pulse traveling along the path 14 which measures the location of the boundary 6, and the other for a sonar pulse traveling along the path 14' which measures the location of the boundary 6'. These measurements are carried out in a manner analogous to that described for the transit time measurements of FIG. 1.

The controller unit 12 is operably connected to the sonar detection stage 11 to receive outputs from the detection stage 11 representative of the two measured transit times. A difference calculation between the locations of the boundaries 6, 6' is made within the controller unit 12. The controller unit 12 is further adapted to calculate the rate of change of location of the boundary with supplied driving force using the calculated difference and from the knowledge of the amplitude of the driving force supplied by the driver 10 to generate the two upper boundary locations 6, 6'. From this rate of change the controller unit 12 generates an estimate of the driving force required to be provided to the oscillator 2 in order to generate a desired degree of nebulization within the nebulizer 1 and controls the driver 10 accordingly.

Although modifications and changes may be suggested by those skilled in the art, it is the intention of the inventor to embody within the patent warranted hereon all changes and modifications as reasonably and properly come within the scope of his contribution to the art.

I claim as my invention:

1. A nebulizer comprising:

a nebulization chamber containing a liquid to be nebulized, said liquid having an upper boundary within said nebulization chamber;

an ultrasonic nebulization source acoustically coupled to said liquid and operable to nebulize said liquid, said ultrasonic nebulization source including a control unit which varies an amplitude of ultrasound produced by said ultrasonic nebulization source to provide at least a first measurement period and a second measurement period during which no nebulization of said liquid occurs, said first and second measurement periods being separated in time from each other;

a sonar device disposed to measure, during each of said first and second measurement periods, a time interval between emission of an acoustic pulse toward said upper boundary and detection of a component of said acoustic pulse reflected from said boundary, and generating respective output signals dependent on said time interval indicative of a location of said upper boundary of said liquid within said nebulization chamber in said first and second measurement periods; and a difference former supplied with said output signals for comparing said output signals to determine a change in the location of said upper boundary of said liquid within said chamber, said difference former emitting a difference former output signal dependent on said difference, said difference former output signal being supplied to said control unit to control at least one of an amplitude and a duration of ultrasound from said ultrasonic nebulization source for nebulizing said liquid within said nebulization chamber.

2. A nebulizer as claimed in claim 1 wherein said sonar device is disposed to emit said acoustic pulse through said liquid to said upper boundary.

3. A nebulizer as claimed in claim 2 wherein said ultrasonic nebulization source comprises a piezoelectric transducer for emitting said ultrasound with a variable amplitude, and wherein said sonar device is also connected to said piezoelectric transducer for emitting and detecting said acoustic pulse during said measurement period.

4. A nebulizer as claimed in claim 1 wherein said ultrasonic nebulization source is operated by said control unit to only emit, during said measurement period, ultrasound having an amplitude which causes substantially no disturbance to said upper boundary of said liquid within said nebulization chamber.

5. A nebulizer as claimed in claim 1 wherein said ultrasonic nebulization source is operated by said control unit during said measurement period to emit ultrasound at a first amplitude for producing a first location of said upper boundary and to emit ultrasound at a second amplitude to produce a different location of said upper boundary, and wherein said sonar device detects a first output signal associated with said first amplitude and a second output signal associated with said second amplitude, and wherein said difference former uses one of said first and second output signals as a reference signal and the other of said first and second output signals as a measurement signal.

6. A nebulizer as claimed in claim 5 wherein said ultrasonic nebulization source is operated by said control unit so that one of said first and second amplitudes produces no disturbance of the location of said upper boundary of said liquid within said nebulization chamber.

7. A nebulizer as claimed in claim 4 wherein said difference former includes a memory connected to said difference former for storing the output signal from said first measurement period.

8. A nebulizer as claimed in claim 7 wherein said difference former derives a difference between signals received from consecutive measurement periods.

* * * * *